US010745337B2

(12) United States Patent
Daliparthi et al.

(10) Patent No.: US 10,745,337 B2
(45) Date of Patent: Aug. 18, 2020

(54) METHOD OF PURIFYING ACETONE

(71) Applicant: SABIC GLOBAL TECHNOLOGIES B.V., Bergen Op Zoom (NL)

(72) Inventors: Surya Prakasa Rao Daliparthi, Karnataka (IN); Nathalie Gonzalez Vidal, Geleen (NL); Paulus Johannes Maria Eijsbouts, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/652,544

(22) PCT Filed: Oct. 3, 2018

(86) PCT No.: PCT/EP2018/076895
§ 371 (c)(1),
(2) Date: Mar. 31, 2020

(87) PCT Pub. No.: WO2019/068752
PCT Pub. Date: Apr. 11, 2019

(65) Prior Publication Data
US 2020/0231526 A1 Jul. 23, 2020

(30) Foreign Application Priority Data
Oct. 6, 2017 (EP) .................................... 17195139

(51) Int. Cl.
*C07C 49/08* (2006.01)
*C07C 45/78* (2006.01)

(52) U.S. Cl.
CPC ............. *C07C 45/78* (2013.01); *C07C 49/08* (2013.01)

(58) Field of Classification Search
CPC ................... C07C 49/08; C07C 45/78
See application file for complete search history.

(56) References Cited

U.S. PATENT DOCUMENTS

| | | | | |
|---|---|---|---|---|
| 2,179,991 A * | 11/1939 | Bright | ...................... | C07C 45/82 203/53 |
| 2,581,789 A * | 1/1952 | Forman | ................... | C07C 29/86 203/70 |
| 2,751,337 A * | 6/1956 | Goddin, Jr. | ........... | C07C 45/783 203/83 |
| 4,584,063 A * | 4/1986 | Berg | ........................ | C07C 29/84 203/51 |
| 6,303,826 B1 * | 10/2001 | Bhinde | ................... | C07C 45/82 568/410 |
| 6,340,777 B1 * | 1/2002 | Aristovich | .............. | C07C 45/82 568/411 |
| 8,143,456 B2 | 3/2012 | Young et al. | | |
| 9,845,277 B2 * | 12/2017 | Nelson | ...................... | B01J 19/24 |
| 10,486,080 B2 | 11/2019 | Choo et al. | | |
| 2011/0137087 A1 * | 6/2011 | Young | ...................... | C07C 29/80 568/728 |
| 2017/0240496 A1 * | 8/2017 | Nelson | ............... | B01D 11/0488 |
| 2018/0169542 A1 * | 6/2018 | Choo | ...................... | C07C 37/08 |
| 2019/0225567 A1 * | 7/2019 | Lee | ........................ | C07C 37/685 |

FOREIGN PATENT DOCUMENTS

| | | | | |
|---|---|---|---|---|
| CN | 104119202 A | * | 10/2014 | |
| EP | 1683779 A1 | * | 7/2006 | ............. C07C 37/20 |
| JP | H09278703 | | 10/1997 | |
| KR | 1020130019667 | * | 8/2011 | |

OTHER PUBLICATIONS

W. Luyben, 37 Ind. Eng. Chem. Res., 2696-2707 (2008) (Year: 2008).*
W. Luyben, 51 Ind. Eng. Chem. Res., 10881-10886 (2012) (Year: 2012).*
G. Modla, 49 Ind. Eng. Chem. Res., 3785-3793 (2010) (Year: 2010).*
English Language Machine Translation KR 1020130019667 (2011) (Year: 2011).*
English Language Machine Translation CN 104119202 (2014) (Year: 2014).*
International Search Report; International Application No. PCT/EP2018/076895; International Filing Date: Oct. 10, 2018; dated Nov. 9, 2018; 5 pages.
Luyben, William L., "Comparison of Extractive Distillation and Pressure-Swing Distillation forAcetone-Methanol Separation", Ind. Eng. Chem. Res., pp. 2696-2707, vol. 47, No. 8, 2008.
Modla et al. , "Separation of an Acetone-Methanol Mixture by Pressure-Swing Batch Distillation in a Double-Column System with and without Thermal Integration", Ind. Eng. Chem. Res., pp. 3785-3793, vol. 49, No. 8, 2010.
Written Opinion; International Application No. PCT/EP2018/076895; International Filing Date: Oct. 10, 2018; dated Nov. 9, 2018; 11 pages.

\* cited by examiner

*Primary Examiner* — Alexander R Pagano
(74) *Attorney, Agent, or Firm* — Cantor Colburn LLP

(57) ABSTRACT

In an embodiment a method of purifying acetone, comprises directing a feed stream comprising greater than or equal to 97 wt % of acetone and 100 to 1,000 ppm of methanol to a separation column, both based on a total weight of the feed stream; separating the feed stream in the separation column that is operating at a pressure greater than or equal to 1 bar into an overhead stream and a purified acetone stream comprising less than or equal to 50 ppm of methanol based on a total weight of the purified acetone stream; and directing at least 80 wt % of the overhead stream into the separation column as a reconstituted stream and purging 1 to 20 wt % of the overhead stream as a purge stream.

19 Claims, 3 Drawing Sheets

METHOD OF PURIFYING ACETONE

CROSS REFERENCE TO RELATED APPLICATIONS

This application is a National Stage application of PCT/EP2018/076895, filed Oct. 3, 2018, which claims the benefit of European Application No. 17195139.5, filed Oct. 6, 2017, both of which are incorporated by reference in their entirety herein.

BACKGROUND

Bisphenol A is commercially produced by the condensation reaction of acetone and two equivalents of phenol in the presence of a catalyst such as an ion-exchange resin. Bisphenol A is a high production volume compound with a world-wide estimated annual production of over 2 million tons. The demand for this compound is primarily due to its use as a monomer in the production of many high commodity materials such as epoxy resins and polycarbonates. Acetone, one of the precursors to bisphenol A, can be formed using the cumene process by reacting benzene and propylene. This reaction disadvantageously forms a methanol by-product that can result in a deactivation of the catalyst system used in the formation of bisphenol. This deactivation requires that the catalyst system be either regenerated or even completely replaced, resulting in production stoppages and additional expenditure in maintaining bisphenol A production facilities.

Separation of acetone-methanol mixtures is very difficult due to the formation of azeotrope at lower pressures. Processes addressing the problems associated with the azeotrope have been developed, including extractive distillation and pressure-swing azeotropic distillation. Separation of methanol from acetone can be achieved with the help of the above mentioned methods, however the separation is especially difficult in compositions initially comprising more than 80 weight percent of acetone due to a low relative volatility between the components at lower pressures. For example, reducing the concentration of methanol from 250 ppm to below 30 ppm conventionally require use of a heavy distillation column.

An improved method for the purification of acetone is therefore desirable.

BRIEF SUMMARY

Disclosed herein is a method of purifying acetone.

In an embodiment a method of purifying acetone, comprises directing a feed stream comprising greater than or equal to 97 wt % of acetone and 100 to 1,000 ppm of methanol to a separation column, both based on a total weight of the feed stream; separating the feed stream in the separation column that is operating at a pressure greater than or equal to 1 bar into an overhead stream and a purified acetone stream comprising less than or equal to 50 ppm of methanol based on a total weight of the purified acetone stream; and directing at least 80 wt % of the overhead stream into the separation column as a reconstituted stream and purging 1 to 20 wt % of the overhead stream as a purge stream.

The above described and other features are exemplified by the following figures and detailed description.

BRIEF DESCRIPTION OF THE DRAWINGS

The following Figures are exemplary embodiments, which are provided to illustrate the present method, wherein the like elements are numbered alike. Several of the figures are illustrative of the examples, which are not intended to limit devices made in accordance with the disclosure to the materials, conditions, or process parameters set forth herein.

DETAILED DESCRIPTION

Figure 1:
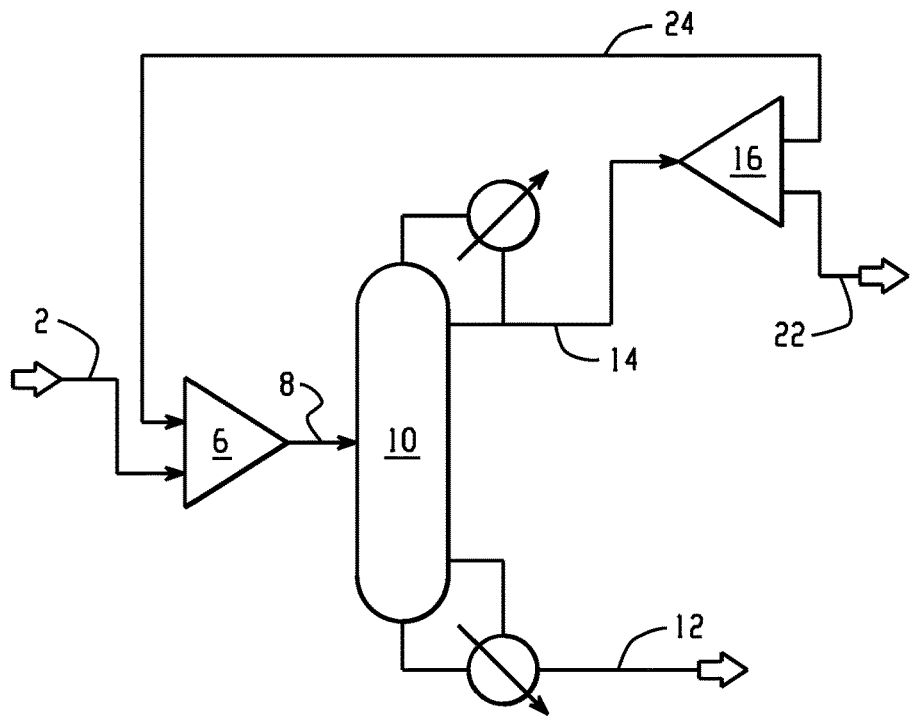
FIG. 1 is an illustration of an embodiment of a method of purifying an acetone stream.

It was surprisingly discovered that more than 60 weight percent (wt %) of the methanol present in the bisphenol A formation reaction originated from fresh, as purchased acetone that was found to comprise 250 parts per million by weight (ppm) methanol based on the total weight of the acetone. Although conventional methods of purifying acetone from methanol, such as extractive distillation and pressure swing distillation that utilize multiple separation columns to separate the azeotropic mixtures of acetone and methanol, are available, reducing the amount of small amounts of methanol, for example, from 250 ppm to less than or equal to 30 ppm is particularly challenging though due to the low relative volatility between the two components at these concentrations. For example, as is described below in Example 1, in order to obtain purified acetone having a low methanol concentration of only 25 ppm of methanol, more than 25 wt % of the feed stream entering distillation column has to be removed in the overhead stream. In other words, in order to achieve a methanol concentration of 25 ppm or less in the purified acetone stream, of a feed stream having a flow rate of 4,000 kilograms per hour (kg/hr) entering the distillation column, more than 25 wt % of the feed stream, or in the case of Example 1, more than 1,000 kg/hr is removed in the overhead stream. This high flow rate of the overhead stream results in significant losses of the acetone in the overhead stream. In this case, all of the overhead stream becomes the purge stream that is either discarded or purified by some other means.

A method of purifying acetone was developed, where it was surprisingly discovered that by directing at least 80 wt % of the overhead stream back into the separation column, a purified acetone stream could be formed comprising less than or equal to 50 ppm of methanol while achieving a significant reduction in the acetone being lost in a purge stream. Specifically, the method of purifying acetone comprises directing a feed stream comprising acetone and methanol to a separation column; separating the feed stream in the separation column that is operating at a pressure greater than or equal to 1 bar into an overhead stream and a purified acetone stream; and directing at least 80 wt % of the overhead stream into the separation column as a reconstituted stream and purging 1 to 20 wt % of the overhead stream as a purge stream.

One cause for the reduction in the acetone being lost in the overhead stream is due to the increase in the methanol concentration in the column as compared to the concentration in a column where only the feed stream is added. This increase in methanol concentration in the column arises because the overhead stream that is directed back into the separation column naturally comprises a higher concentration of methanol than the feed stream due to the separation process. The fact that the concentration of methanol in the column is higher with the addition of the reconstituted stream, results in the concentration of methanol in both the overhead stream and the purge stream also being higher (for example, the 1.3 wt % of Example 2), as compared to Example 1 (905 ppm methanol), where portion of the overhead stream is not directed back into the separation column. In comparing these two examples, it is observed that while the amount of methanol initially added to the separation column via a feed stream is the same, the concentration of the methanol in the purge stream is different. As a result, directing the reconstituted stream to the separation column has the downstream effect of increasing the concentration of the methanol in the purge stream, resulting in a reduced amount of acetone lost in the purge stream in order to achieve the same reduced concentration of methanol in the purified acetone stream. Without being bound by theory, it is also believed that this increased concentration of methanol in the purge stream and the resulting improved separation arises due to an increased driving force for mass transfer.

It was also found that separation of the methanol from the acetone could be further enhanced by increasing the pressure in the separation column as increasing the pressure of the separation column shifts the azeotrope to a lower acetone mass fraction and enhances the relative volatility between the components on the right of the azeotropic composition, facilitating a more efficient separation at higher mass fractions. It was found, for example, that at pressure of greater than or equal to 3 bars, or 3 to 15 bars that good separation of the two components can occur at high mass fractions of acetone of greater than 0.6, or 0.6 to 0.98, or 0.7 to 0.95, or 0.75 to 0.95.

FIG. 1 is an illustration of an embodiment of a method of purifying an acetone stream. In FIG. 1, feed stream 2 and reconstituted stream 24 are combined in junction 6 to form combined stream 8 that is directed to separation column 10. It is noted that while feed stream 2 and reconstituted stream 24 are illustrated as being combined prior to addition to separation column 10, they can likewise be added as separate streams. Examples of junction 6 include T-joints, Y-joints, and static mixers.

The feed stream can comprise greater than or equal to 97 wt %, or 97 to 99.99 wt %, or 98 to 99.5 wt % of acetone based on the total weight of the feed stream. The feed stream can comprise 100 to 5,000 ppm, or 100 to 500 ppm, or 200 to 300 ppm of methanol based on the total weight of the feed stream. The feed stream can comprise less than or equal to 5 wt %, or 0 to 1 wt %, or 0 to 0.9 wt % of water based on the total weight of the feed stream.

The separation column can be a distillation column. The column can operate at a reflux ratio of 1 to 100, or 10 to 55, or 10 to 35, or 1 to 20. The column can comprise 6 to 80 stages, or 25 to 45 stages or packing equivalent to said number of stages. At least two streams can exit the separation column including purified acetone stream 12 and overhead stream 14. The purified acetone stream can comprise 1 to 40 ppm, or 5 to 25 ppm of methanol based on the total weight of the purified acetone stream.

Overhead stream 14 is split into reconstituted stream 24 and purge stream 22 in splitter 16. Examples of splitter 16 include a T-joint and a Y-joint, optionally with a valve to control the respective flow rates. At least 80 wt %, or 90 to 97 wt %, or 80 to 99 wt % of the overhead stream is directed back into the separation column as reconstituted stream 24. At least 1 wt %, or 1 to 20 wt %, or 3 to 10 wt % of the overhead stream is purged from the system as purge stream 22.

Although the present method significantly reduces the amount of acetone lost from the overhead stream, by directing at least 80 wt % of the overhead stream back into the separation column as a reconstituted stream, an amount of acetone is lost in the purge stream. For example, a purge stream having a flow rate of 65 kg/hr and comprising 98 wt % or more of acetone, can result in a loss of more than 63 kg/hr of acetone. It was discovered that this acetone could be recovered by directing the purge stream to a phenol water separation (PWS) unit.

The phenol water separation unit can comprise a series of separation units including an extraction column that utilizes an organic phase and an aqueous phase to extract the phenol and acetone into the organic phase. The organic phase can comprise an organic solvent, for example, at least one of methyl isobutyl ketone, butanone, pentanone, hexanone, heptanone, methyl acetate, ethyl acetate, butyl acetate, methyl isopropyl ketone, benzene, toluene, ethyl benzene, and xylene. The organic phase can then be treated in a series of distillation columns to separate the acetone and phenol. The aqueous phase can be directed to a stripper column where the acetone can be stripped out and sent to one or more distillation columns for further separation and the methanol can be purged with the waste water.

For example, in the phenol water separation unit, at least a portion of the acetone can be separated into the organic phase and can return back to extraction column along with any recovered solvent. At least a portion of the acetone can be separated into the raffinate phase (aqueous phase) and can be sent to a stripper column where the acetone can be stripped out along with some water. Most of the methanol can be removed with the bottoms of the stripper column and can be directed towards a waste water recovery section. The stripped out acetone water mixture can be directed to an acetone column where acetone product can be recovered. A small portion of the total methanol can remain with the acetone product out of the phenol water separation unit and can be recycled back to a high pressure distillation column along with a fresh acetone feed.

Figure 2:
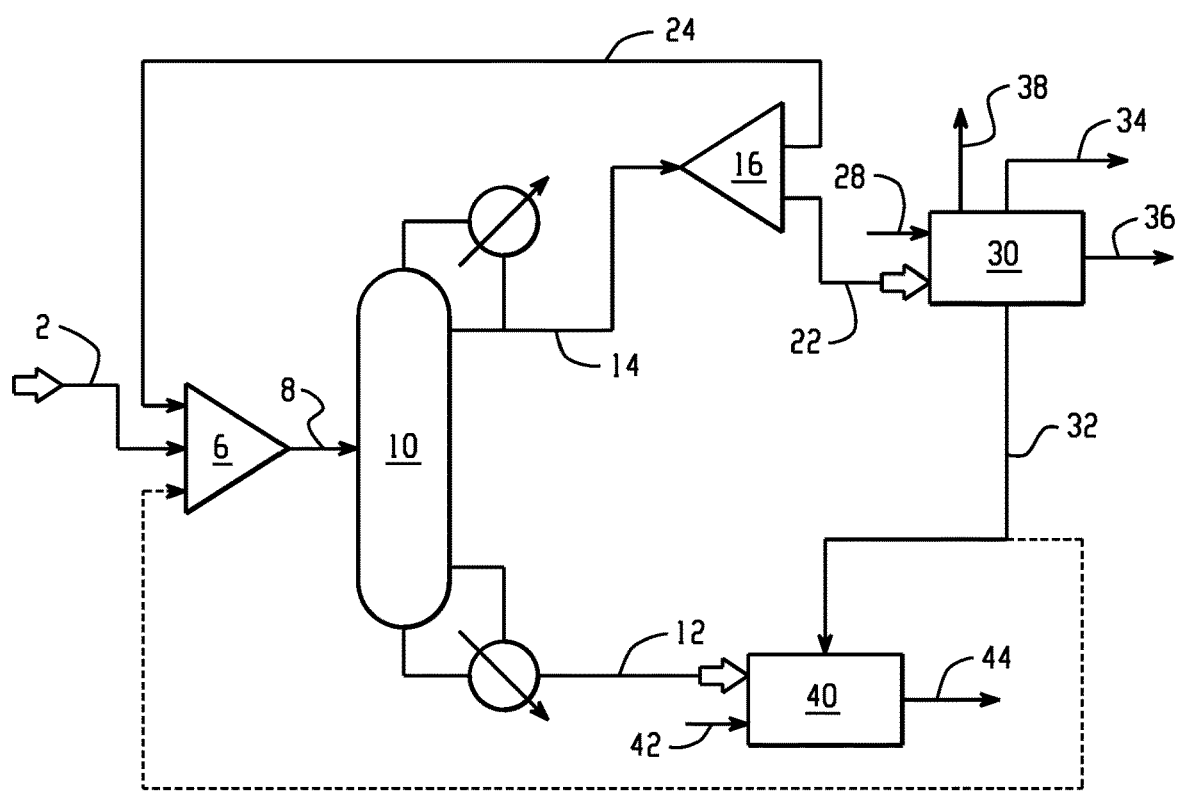
FIG. 2 is an illustration of another embodiment of a method of purifying an acetone stream.

An example of integration of the purge stream with a PWS unit is illustrated in FIG. 2. Here, purge stream 22 and PWS feed stream 28 are directed to PWS unit 30. Acetone can be recovered from one or both of vent stream 38 and recovered acetone stream 32. At least a portion of one or both of vent stream 38 and recovered acetone stream 32 can be directed to bisphenol production facility 40. At least a portion of one or both of vent stream 38 and recovered acetone stream 32, for example, 95 to 100 wt %, or 100 wt % of each stream independently, can be directed to separation column 10. Vent stream 38 and recovered acetone stream 32 can each independently comprise 90 to 100 wt %, or 95 to 99.5 wt % of acetone based on the total weight of the respective streams.

Waste water stream 34 can be removed from PWS unit 30 and can comprise greater than or equal to 90 wt %, or 93 to 99 wt % of the total methanol that was introduced to PWS unit 30. Phenol stream 36 can be removed from PWS unit. Phenol stream 36 can be directed to bisphenol production facility 40. Phenol stream 36 can be directed to a carbonate compound production facility, for example, to form diphenyl carbonate.

The purified acetone stream can be directed to a bisphenol production facility. For example, the purified acetone stream can be in direct fluid communication with a reactor in a bisphenol production facility for immediate use. Conversely, the purified acetone stream can be in fluid communication with a storage unit, stored for an amount of time, optionally transported, and then the stored purified acetone can be directed to a reactor in a bisphenol production facility. The purified acetone stream can be added directly to the bisphenol production facility such that the purified acetone stream is not further purified in a purification step intervening the separation column 10 and the bisphenol production facility. In other words, the concentration of the purified acetone stream exiting the separation column can be the same (i.e., within 1 wt %) of the purified acetone stream entering the bisphenol production facility. The bisphenol production facility can be a bisphenol A production facility.

The purified acetone stream can be combined with a monomer feed stream comprising a phenolic compound such as phenol and reacted to form a bisphenol. FIG. 2 illustrates an embodiment of such a method, where purified acetone stream 12 and phenolic feed stream 42 are directed to bisphenol production facility 40 that produces bisphenol stream 44. The bisphenol reaction can comprise reacting the acetone and a phenolic compound in the presence of a catalyst system comprising an ion-exchange resin with an attached promotor. The bisphenol reaction of the acetone and phenolic compound can occur in a stoichiometric amount or in a molar excess of the phenolic compound. For example, the molar ratio of the phenolic compound to the acetone can be 20:1 to 2:1. The bisphenol reaction can occur at a temperature of 40 to 150° C., or 55 to 100° C. with, for example, 1 to 40 wt % catalyst based on the weight of the phenolic compound and the acetone. The bisphenol reaction can occur at a weight hourly space velocity (WHSV) of 0.2 to 30 inverse hours ($hr^{-1}$), or 0.5 to 20 $hr^{-1}$.

The catalyst system for the bisphenol reaction can comprise and ion-exchange resin comprising a sulfonated copolymer product of a monovinyl aromatic monomer and a polyvinyl aromatic monomer, for example, having less than 2 wt % crosslinking, and 0.1 to 1.0 millimoles (mmol), or 0.4 to 0.6 mmol of sulfone bridges per gram of dry catalyst. As used herein the term "dry catalyst" can refer to a catalyst with a water content of less than or equal to 1 wt %, or less than or equal to 0.1 wt % of water based on the total weight of the catalyst. The catalyst system can comprise an ion-exchange resin comprising a plurality of sulfonic acid sites; and 5 to 35 mole percent (mol %) of an attached promoter molecule based on the total moles of the sulfonic acid sites in the catalyst system; and wherein the attached promoter molecule can comprise at least two thiol groups per attached promoter molecule. A bulk promoter can be present in the bisphenol reaction.

After formation of the bisphenol, the product mixture can be post-treated to purify the bisphenol. The post-treatment can comprise crystallization of bisphenol to form crystals comprising a crystallized bisphenol and/or a crystallized bisphenol adduct. The crystallization can comprise a vacuum cooling step. The crystallization can be facilitated by adding water, for example, in an amount of less than or equal to 3 wt %, or 0.1 to 3 wt % based on the total weight of the product mixture. The crystals can be optionally separated, for example, by filtration and melted in a melting unit. If the melt comprises sulfur, then a base (such as sodium hydroxide and potassium hydroxide) can be added to the melt to form a melt stream with a reduced sulfur content. The melted stream can be filtered, further purified, and then solidified, for example, in a flaking unit.

The produced bisphenol can have the formula (3)

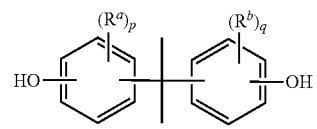

(3)

wherein $R^a$ and $R^b$ are each independently a halogen, $C_{1-12}$ alkoxy, or $C_{1-12}$ alkyl; and p and q are each independently integers of 0 to 4. The bisphenol can comprise bisphenol A.

The bisphenol produced then can be used to manufacture a polycarbonate having repeating structural carbonate units of formula (1)

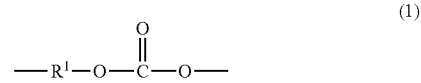

(1)

in which the $R^1$ group is derived from the bisphenol.

The following examples are provided to illustrate the present method. The examples are merely illustrative and are not intended to limit devices made in accordance with the disclosure to the materials, conditions, or process parameters set forth therein.

EXAMPLES

Example 1: Separation Without a Recycle Stream

A simulation using ASPEN software was performed where an acetone feed stream comprising acetone and 250 ppm of methanol was added to a distillation column. The flow rate of the acetone feed stream was 4,000 kilograms per hour (kg/hr) and the distillate to feed weight ratio was 0.25. The column had 20 stages, a reflux ratio of 20, and operated at a pressure of 1 bar. The amount of overhead stream withdrawn from the top of the column was varied and the concentration of the methanol in the purified acetone stream was determined. The results are illustrated in FIG. 3.

Figure 3:
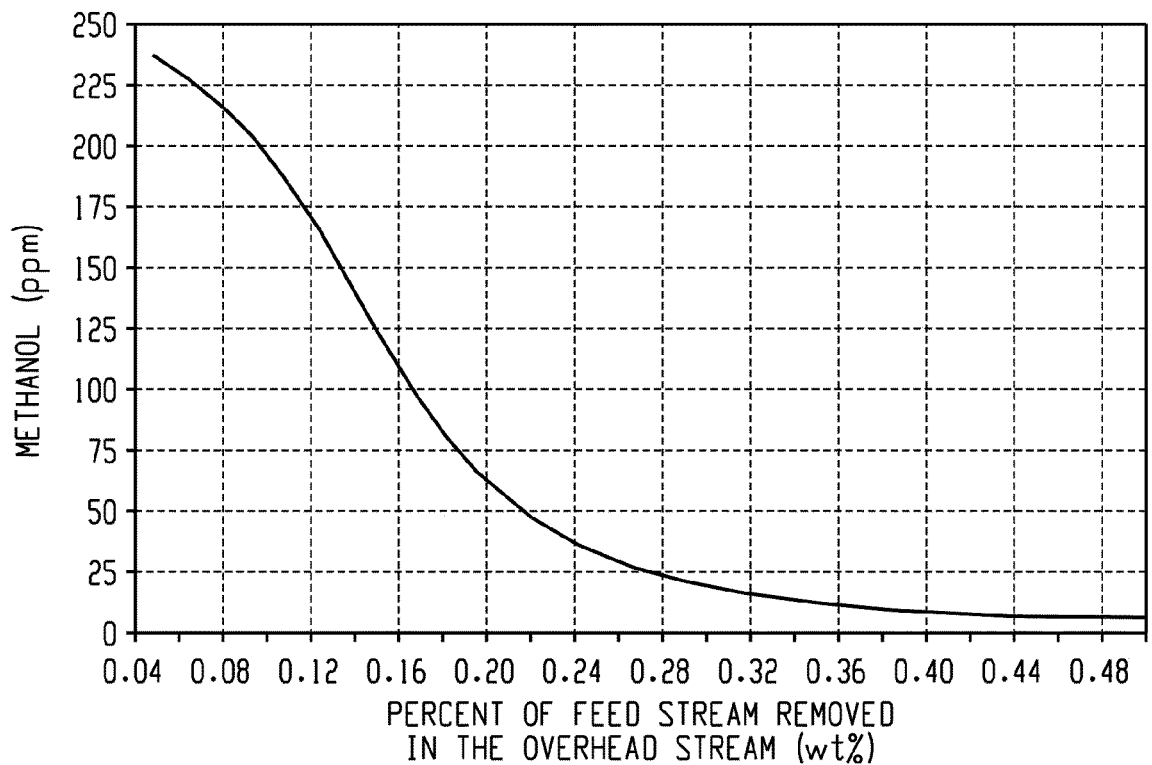
FIG. 3 is a graphical illustration of the effect of the amount of overhead withdrawn on the methanol concentration of the purified acetone stream of Example 1.

FIG. 3 illustrates that in order to achieve a methanol concentration of 25 ppm or less in the purified acetone stream, more than 25 wt % of the feed stream entering distillation column has to be removed in the overhead stream. In other words, to achieve a methanol concentration of 25 ppm or less in the purified acetone stream, of the 4,000 kg/hr entering the distillation column, more than 25% of the feed stream, or in this case, more than 1,000 kg/hr is removed in the overhead stream as a purge stream that requires a separate purification process. The concentration of methanol in the purge stream was 905 ppm.

Further simulations were performed to show that by varying the reflux ratio from 15 to 25 and the number of stages from 15 to 30, the amount of methanol in the purified acetone stream only varies from 27 to 52 ppm as is shown in Table 1.

TABLE 1

|  | Example | | | | |
| --- | --- | --- | --- | --- | --- |
|  | 1A | 1B | 1C | 1D | 1E |
| Reflux ratio | 20 | 15 | 15 | 25 | 25 |
| Number of stages | 20 | 20 | 30 | 15 | 18 |
| Methanol in the purified acetone stream (ppm) | 32 | 52 | 27 | 46 | 30 |

Example 2: Separation With a Recycle Stream

A separation simulation was performed in accordance with Example 1, except that 95 wt % of the overhead stream was redirected back into the distillation column according to FIG. 1 and with 30 number of stages using a reflux ratio of 35. The mass flow and components of the streams are shown in Table 2.

TABLE 2

| Stream | Feed Stream | Purge Stream | Overhead Stream | Combined Stream | Purified Stream |
| --- | --- | --- | --- | --- | --- |
| Stream number | 2 | 22 | 14 | 8 | 12 |
| Vapor Fraction | 1 | 0 | 0 | 0.77 | 0 |
| Total mass flow rate (kg/hr) | 4,000 | 65.5 | 1,311.5 | 5,246.0 | 3,934.5 |
| Acetone (kg/hr) | 3,999 | 64.7 | 1,294.0 | 5,228.3 | 3,934.3 |
| Methanol (kg/hr) | 1 | 0.9 | 17.5 | 17.6 | 0.1 |
| Methanol (mass fraction/ ppm) | 0.000/250 | 0.013 | 0.013 | 0.003 | 0.000/32 |

Table 2 shows that by redirecting 95 wt % of the overhead stream 14 back into the distillation column as reconstituted stream 24, that the amount of overhead stream purged from the system was reduced from 1,000 kg/hr to only 65.6 kg/hr while achieving a low concentration of methanol in the acetone stream of 32 ppm.

Example 3: Effect of Varying the Amount of the Overhead Stream Reconstitution

The simulation of Example 2 was performed by varying the mass fraction of the overhead stream that was reconstituted by redirection back into the distillation column from 0.90 to 0.98. The reflux ratio and the amount of acetone in the purge stream in kg/hr was determined and the results are presented in FIG. 4.

Figure 4:
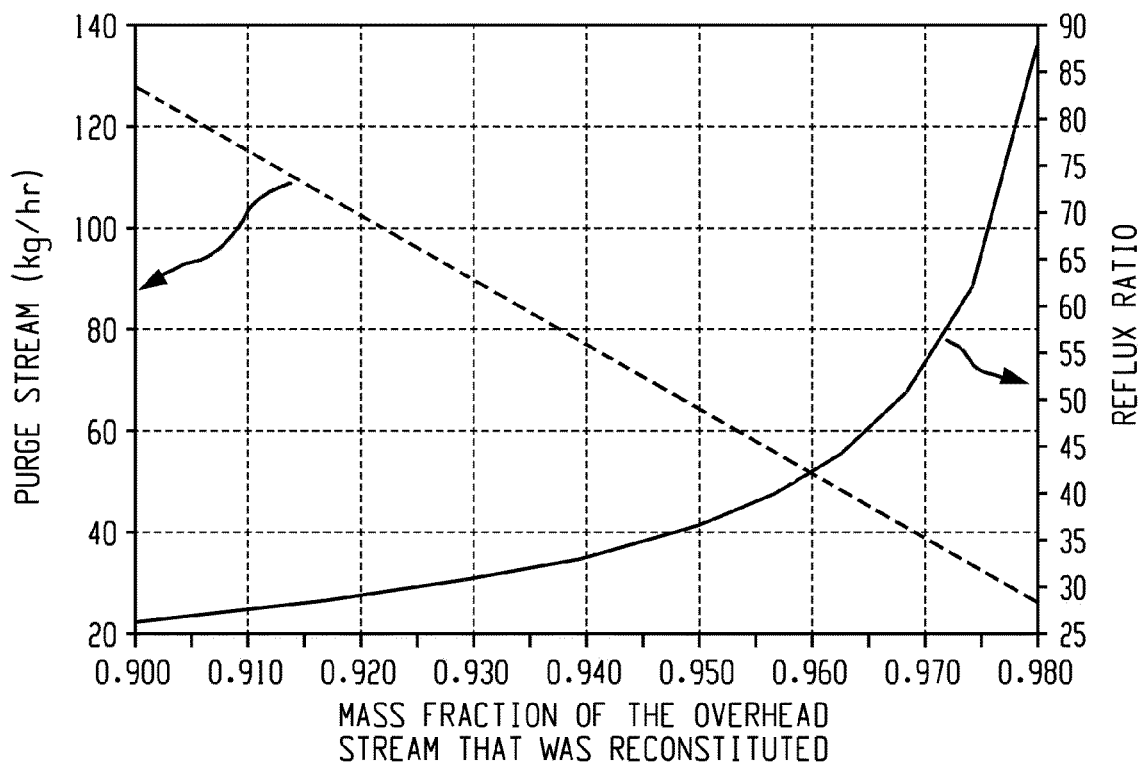
FIG. 4 is a graphical illustration of the effect of changing the reconstitution amount of the overhead stream of Example 3 when the separation column is operated at 1 bar.

FIG. 4 shows that increasing the amount of the overhead stream 14 that is recycled back to the column as reconstituted stream 24 results in a beneficial decrease in the acetone lost in the purge stream 22. As the amount of overhead stream that is recycled back to the column as reconstituted stream 24 increases though, for example, to above 97%, the reflux ratio begins to increase at a fast rate and can result in an undesirable increase in both capital costs and operating costs.

Example 4: Effect of Varying the Pressure in Distillation Column

Figure 5:
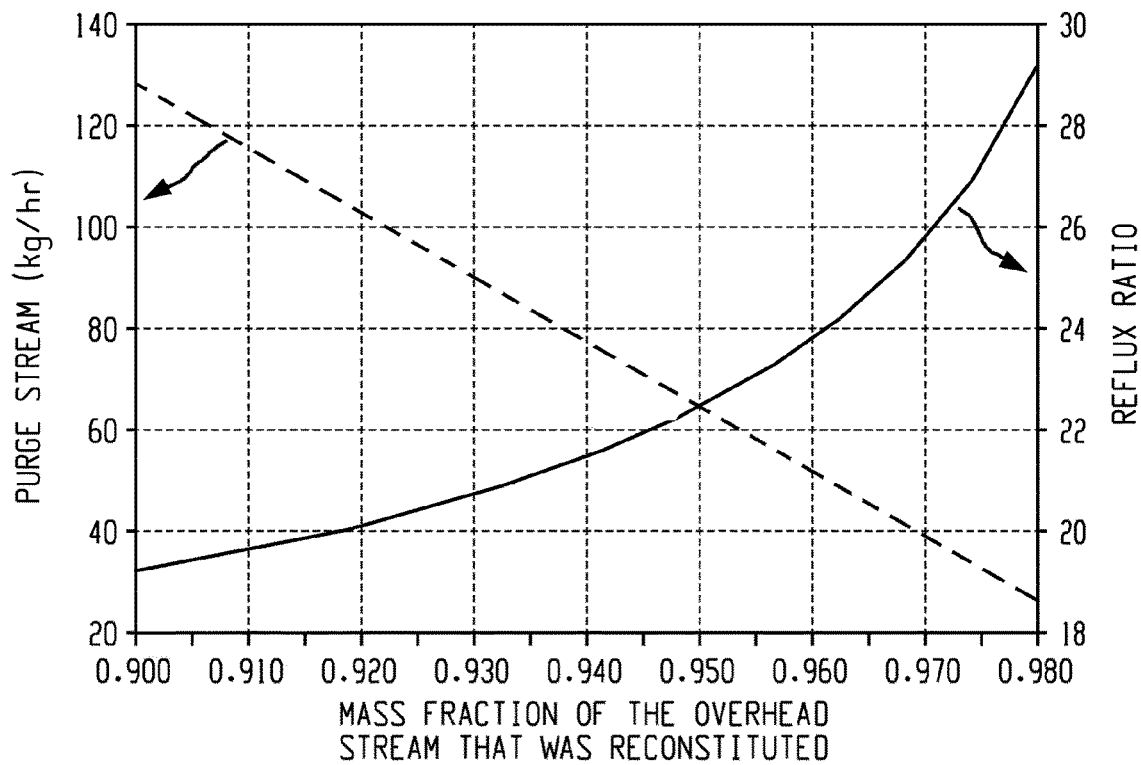
FIG. 5 is a graphical illustration of the effect of changing the reconstitution amount of the overhead stream of Example 4 when the separation column is operated at 5 bars.

The simulation of Example 3 was performed, except that the pressure in the column was 5 bars and the number of stages was 40. Experimentally generated high pressure vapor-liquid equilibrium data (VLE data) was used for ASPEN simulations, from the article "Wilsak, R. A.; Campbell, S. W.; Thodos, G. Fluid Phase Equilib., 1986, 28, 13 Vapor-liquid equilibrium measurements for the methanol-acetone system at 372.8, 397.7 and 422.6 K". The reflux ratio and the amount of acetone in the purge stream in kg/hr was determined and the results are presented in FIG. 5. FIG. 5 shows that at a 95 wt % reconstitution rate, the concentration of the methanol in the purified acetone stream was 30 ppm and that that reflux ratio was surprisingly reduced from 35 to only 22.4, resulting in a significant savings in operating costs.

Example 5: Effect of Varying the Pressure in Distillation Column

Figure 6:
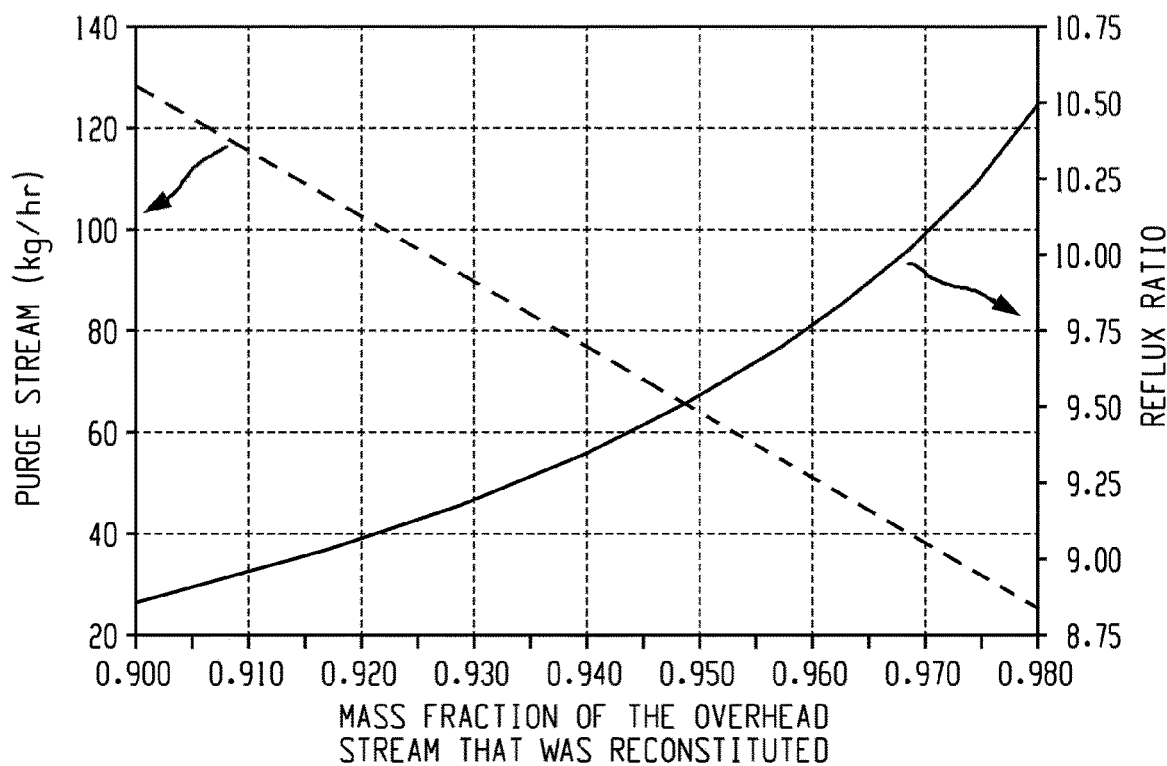
FIG. 6 is a graphical illustration of the effect of changing the reconstitution amount of the overhead stream of Example 5 when the separation column is operated at 15 bars.

The simulation of Example 4 was performed, except that the pressure in the column was 15 bars. The reflux ratio and the amount of acetone in the purge stream in kg/hr was determined and the results are presented in FIG. 6. FIG. 6 shows that at a 95 wt % reconstitution rate, the concentration of the methanol in the purified acetone stream was 30 ppm and that that reflex ratio was further reduced to only 9.5, resulting in further savings in operating costs.

Example 6: Integration of Acetone Purification Unit With a PWS Unit

Separation of acetone from a purge stream 22 was performed using the phenol water separation unit as illustrated in FIG. 2. Here, purge stream 22 as presented in Table 2 was added with PWS feed stream 28 and separated into vent stream 38, waste water stream 34, phenol stream 36, and recovered acetone stream 32. The components of streams 22, 28, 38, 34, and 32 are shown in Table 3.

TABLE 3

| Stream | PWS Inlet Streams | Recovered Acetone Stream | Vent Stream | Waste Water Stream |
| --- | --- | --- | --- | --- |
| Stream number | 22 + 28 | 32 | 38 | 34 |
| Acetone (kg/hr) | 152.9 | 73 | 79.2 | 0.7 |
| Methanol (kg/hr) | 2.04 | 0.03 | 0.08 | 1.93 |

Table 3 shows that 73 kg/hr of acetone are recovered in recovered acetone stream 32 and 79 kg/hr of acetone are recovered in vent stream 38. Table 3 also shows that waste water stream 34 contains about 95 wt % of the total methanol added to the PWS unit and less than 0.5 wt % of the total acetone added to the PWS unit. As the recovered acetone stream 32 and vent stream 38 contain less than 780 ppm of methanol (which is about 5 wt % of the total methanol), at least a portion of one or both of these streams can be sent to a bisphenol A reactor and the remaining portion can be recycled back to separation column 10.

Set forth below are non-limiting embodiments of the present disclosure.

Embodiment 1: A method of purifying acetone, comprising: directing a feed stream comprising greater than or equal to 97 wt % of acetone and 100 to 1,000 ppm of methanol to a separation column, both based on a total weight of the feed stream; separating the feed stream in the separation column that is operating at a pressure greater than or equal to 1 bar into an overhead stream and a purified acetone stream comprising less than or equal to 50 ppm of methanol based on a total weight of the purified acetone stream; and directing at least 80 wt % of the overhead stream into the separation column as a reconstituted stream and purging 1 to 20 wt % of the overhead stream as a purge stream.

Embodiment 2: The method of Embodiment 1, wherein the feed stream comprises 97 to 99.5 wt %, or 98 to 99.5 wt % of acetone based on the total weight of the feed stream.

Embodiment 3: The method of any one of the preceding embodiments, wherein the feed stream comprises 100 to 500 ppm, or 200 to 300 ppm of methanol based on the total weight of the feed stream.

Embodiment 4: The method of any one of the preceding embodiments, wherein the pressure is 3 to 20 bars, or 5 to 20 bars.

Embodiment 5: The method of any one of the preceding embodiments, wherein the pressure is 5 to 15 bars.

Embodiment 6: The method of any one of the preceding embodiments, wherein the purified acetone stream comprises 1 to 40 ppm of methanol based on the total weight of the purified acetone stream.

Embodiment 7: The method of any one of the preceding embodiments, wherein the directing the overhead stream comprises directing 90 to 97 wt % of the overhead stream into the separation column.

Embodiment 8: The method of any one of the preceding embodiments, wherein the purging comprises purging 3 to 10 wt % of the overhead stream as purge stream.

Embodiment 9: The method of any one of the preceding embodiments, wherein the column operates at a reflux ratio of less than or equal to 35, or 1 to 20.

Embodiment 10: The method of any one of the preceding embodiments, further comprising combining the feed stream and the reconstituted stream upstream of the separation column to form a combined stream and directing the combined stream to the separation column.

Embodiment 11: The method of any one of the preceding embodiments, further comprising adding the purified acetone stream and a monomer feed stream comprising phenol to a bisphenol production facility and forming a bisphenol stream in the bisphenol production facility.

Embodiment 12: The method of Embodiment 11, further comprising directly adding the purified acetone stream such that it is not further purified prior to the adding.

Embodiment 13: The method of any one of the preceding embodiments, further comprising directing the purge stream and a phenol water feed stream to a phenol water separation unit and separating a waste water stream, a phenol stream, and a recovered acetone stream.

Embodiment 14: The method of Embodiment 13, further comprising directing at least a portion of the recovered acetone stream to the separation column.

Embodiment 15: The method of any one of the Embodiments 13 to 14, further comprising directing at least a portion of the recovered acetone stream to the bisphenol production facility of any one of Embodiments 11 to 12.

Embodiment 16: The method of any one of the Embodiments 13 to 15, wherein greater than or equal to 99 wt % of the acetone in the purge stream is recovered in the recovered acetone stream.

Embodiment 17: The method of any one of the Embodiments 13 to 16, wherein the recovered acetone stream is recycled back to one or both of a bisphenol A production facility and an acetone purification unit.

Embodiment 18: The method of any one of the preceding embodiments, wherein the feed stream comprises less than or equal to 5 wt %, or 0 to 1 wt %, or 0 to 0.9 wt % of water based on the total weight of the feed stream.

Embodiment 19: The method of any one of the preceding embodiments, wherein the purified acetone stream comprises 5 to 25 ppm of methanol based on the total weight of the purified acetone stream.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

The terms "a" and "an" do not denote a limitation of quantity, but rather denote the presence of at least one of the referenced item. The term "or" means "and/or" unless clearly indicated otherwise by context. Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

The endpoints of all ranges directed to the same component or property are inclusive of the endpoints, are independently combinable, and include all intermediate points and ranges. For example, ranges of "up to 25 wt %, or 5 to 20 wt %" is inclusive of the endpoints and all intermediate values of the ranges of "5 to 25 wt %," such as 10 to 23 wt %, etc. Unless otherwise mentioned, all weight percent values of a component in a stream are based on the total weight of the respective stream.

The term "combination" is inclusive of blends, mixtures, alloys, reaction products, and the like. Also, "combinations comprising at least one of the foregoing" means that the list is inclusive of each element individually, as well as combinations of two or more elements of the list, and combinations of at least one element of the list with like elements not named.

Unless defined otherwise, technical and scientific terms used herein have the same meaning as is commonly understood by one of skill in the art to which this disclosure belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of purifying acetone, comprising: directing a feed stream comprising greater than or equal to 97 wt % of acetone and 100 to 1,000 ppm of methanol to a separation column, both based on a total weight of the feed stream; separating the feed stream in the separation column, that is operating at a pressure greater than or equal to 1 bar, into an overhead stream and a purified acetone stream comprising less than or equal to 50 ppm of methanol based on a total weight of the purified acetone stream; removing the purified acetone stream; and directing at least 80 wt % of the overhead stream into the separation column as a reconstituted stream and purging 1 to 20 wt % of the overhead stream as a purge stream.

2. The method of claim 1, further comprising directing the purge stream and a phenol water feed stream to a phenol water separation unit and separating a waste water stream, a phenol stream, and a recovered acetone stream.

3. The method of claim 1, wherein the feed stream comprises 97 to 99.5 wt % of acetone based on the total weight of the feed stream.

4. The method of claim 1, wherein the feed stream comprises 100 to 500 ppm of methanol based on the total weight of the feed stream.

5. The method of claim 1, wherein the pressure is 3 to 20 bars.

6. The method of claim 1, wherein the pressure is 5 to 15 bars.

7. The method of claim 1, wherein the purified acetone stream comprises 1 to 40 ppm of methanol based on the total weight of the purified acetone stream.

8. The method of claim 1, wherein the directing the overhead stream comprises directing 90 to 97 wt % of the overhead stream into the separation column.

9. The method of claim 1, wherein the purging comprises purging 3 to 10 wt % of the overhead stream as purge stream.

10. The method of claim 1, wherein the column operates at a reflux ratio of less than or equal to 35.

11. The method of claim 1, further comprising combining the feed stream and the reconstituted stream upstream of the separation column to form a combined stream and directing the combined stream to the separation column.

12. The method of claim 1, further comprising adding the purified acetone stream and a monomer feed stream comprising phenol to a bisphenol production facility and forming a bisphenol stream in the bisphenol production facility.

13. The method of claim 12, further comprising directly adding the purified acetone stream such that it is not further purified prior to the adding.

14. The method of claim 13, further comprising directing at least a portion of the recovered acetone stream to the separation column.

15. The method of claim 13, further comprising directing at least a portion of the recovered acetone stream to a bisphenol production facility.

16. The method of claim 13, wherein greater than or equal to 99 wt % of the acetone in the purge stream is recovered in the recovered acetone stream.

17. The method of claim 13, wherein the recovered acetone stream is recycled back to one or both of a bisphenol A production facility and an acetone purification unit.

18. The method of claim 1, wherein the feed stream comprises less than or equal to 5 wt % of water based on the total weight of the feed stream.

19. The method of claim 1, wherein the purified acetone stream comprises 5 to 25 ppm of methanol based on the total weight of the purified acetone stream.

* * * * *